(12) United States Patent
Iwashita et al.

(10) Patent No.: US 8,919,359 B2
(45) Date of Patent: Dec. 30, 2014

(54) METHOD FOR STERILIZING A CONTAINER AND 3-FLUID NOZZLE USED FOR CARRYING OUT THE METHOD

(75) Inventors: Takeshi Iwashita, Kanagawa (JP);
Kenichi Kominami, Kanagawa (JP);
Chikako Sunohara, Kanagawa (JP);
Miki Hirabayashi, Kanagawa (JP)

(73) Assignee: Toyo Seikan Kaisha, Ltd., Tokyo (JP)

( * ) Notice: Subject to any disclaimer, the term of this patent is extended or adjusted under 35 U.S.C. 154(b) by 0 days.

(21) Appl. No.: 13/820,749

(22) PCT Filed: Sep. 15, 2011

(86) PCT No.: PCT/JP2011/071072
§ 371 (c)(1),
(2), (4) Date: Mar. 4, 2013

(87) PCT Pub. No.: WO2012/046555
PCT Pub. Date: Apr. 12, 2012

(65) Prior Publication Data
US 2013/0183196 A1  Jul. 18, 2013

(30) Foreign Application Priority Data

Oct. 7, 2010 (JP) ................................. 2010-227321

(51) Int. Cl.
| | | |
|---|---|---|
| *B08B 3/00* | (2006.01) | |
| *F16K 31/18* | (2006.01) | |
| *F26B 21/06* | (2006.01) | |
| *B65B 43/42* | (2006.01) | |
| *B65D 88/54* | (2006.01) | |
| *F02M 41/16* | (2006.01) | |
| *A61L 2/20* | (2006.01) | |
| *B65B 55/10* | (2006.01) | |
| *B05B 1/02* | (2006.01) | |
| *A61L 2/22* | (2006.01) | |

(52) U.S. Cl.
CPC ................ *A61L 2/208* (2013.01); *B65B 55/10* (2013.01); *B05B 1/02* (2013.01); *A61L 2/22* (2013.01); *A61L 2202/23* (2013.01)
USPC ........... 134/179; 134/129; 134/148; 137/438; 34/541; 34/638; 141/177; 141/208; 141/296; 22/321.6; 239/87; 239/270; 239/311; 239/422; 239/408

(58) Field of Classification Search
CPC ............. A61L 2/00; A61L 2/208; B05C 1/00; B05B 12/14
USPC ........... 422/1, 28, 32, 38; 134/6, 22.1, 32, 34, 134/129, 148, 24, 179; 137/438; 34/541, 34/638; 141/177, 208, 296; 222/321.6; 239/87, 95–96, 270, 311, 422, 408
See application file for complete search history.

(56) References Cited

U.S. PATENT DOCUMENTS

2008/0107562 A1* 5/2008 Hayashi et al. ................. 422/28

FOREIGN PATENT DOCUMENTS

| CN | 1051509 A | 5/1991 |
|---|---|---|
| CN | 1146916 A | 4/1997 |

(Continued)

OTHER PUBLICATIONS

Limin, Hao, "Notification of First Office Action and Search Report for Chinese Patent Application No. 201180046760.0," State Intellectual Property Office of the People's Republic of China, Dec. 4, 2013.

(Continued)

*Primary Examiner* — Monzer R Chorbaji
(74) *Attorney, Agent, or Firm* — Florek & Endres PLLC

(57) ABSTRACT

For reducing time required for sterilizing a container by hydrogen peroxide, mitigating a cost required therefore, simplifying a sterilizing apparatus, reducing space for installing such apparatus, and mitigating load to the environment, a method for sterilizing a container is provided according to which hydrogen peroxide aqueous solution, air at the normal temperature and hot air are simultaneously injected into a container whereby the hydrogen peroxide aqueous solution which has been turned to minute droplets by the air at the normal temperature is instantly gasified.

1 Claim, 2 Drawing Sheets

(56) References Cited

FOREIGN PATENT DOCUMENTS

| | | |
|---|---|---|
| CN | 1281374 A | 1/2001 |
| CN | 1336829 A | 2/2002 |
| CN | 1547540 A | 11/2004 |
| CN | 101460261 A | 6/2009 |
| JP | 2009113858 A | 5/2009 |

OTHER PUBLICATIONS

Hwan, Jeong Se, "Office Action for Korean Patent Application No. 10-2013-7003418," Korean Intellectual Property Office, First Patent Examination Department, Sep. 15, 2014.

* cited by examiner

METHOD FOR STERILIZING A CONTAINER AND 3-FLUID NOZZLE USED FOR CARRYING OUT THE METHOD This application is a U.S. National Stage filing under 35 U.S.C. 371 of International Application No. PCT/JP2011/071072, filed Sep. 15, 2011, which in turn claims priority to Japanese Patent Application No. 2010-227321, filed Oct. 7, 2010.

TECHNICAL FIELD

This invention relates to a method for sterilizing containers including polyester containers such as a PET bottle and other types of containers and a 3-fluid nozzle used for carrying out the method.

BACKGROUND ART

The aseptic filling system is a system according to which a container such as a bottle in which a drink is to be filled as well the drink are sterilized and the drink is filled in the sterilized container in a sterilized environment. As a method for sterilizing a container is widely used a method of sterilizing a container by using hydrogen peroxide aqueous solution or hydrogen peroxide mist and thereafter washing the container by using sterilized water or hot air. In the aseptic filling system, amounts of sterilizing agent and sterilized water for washing are determined depending upon a line construction of the aseptic filling system. As the line speed is increased, amounts of supply of the sterilizing agent and the sterilized water to the line per unit time are also increased which causes the problems that initial cost and running cost are increased, the sterilizing apparatus and space for installing such apparatus become larger, and load to the environment increases. In particular, in a case where a container is sterilized by using hydrogen peroxide mist in the aseptic filling system, it is necessary to heat and thereby vaporize hydrogen peroxide aqueous solution and then condense the vaporized hydrogen peroxide to produce hydrogen peroxide mist and, for this purpose, an apparatus for generating mist must be installed in the system. This not only increases the size of the system but also requires, for example, about 8 seconds for sterilizing the inner surface of a single PET bottle of 500 ml with resulting increase in the line speed and requirement for two or more turrets for sterilization in the sterilizing system in which a large number of PET bottles are sterilized while they are moved on these turrets. The reason for requiring about 8 seconds for sterilizing the inner surface of a single PET bottle is that, as the PET bottle becomes thinner, projections and depressions in a reinforcing bead of the bottle, for example, increase for maintaining or reinforcing the configuration of the bottle and hence it requires sufficient time for each minute droplet of hydrogen peroxide mist which is an aggregate of minute droplets to scatter to reach all surfaces of such projections and depression and to be deposited on the inner surface of the bottle uniformly. Patent Literature 1 discloses a method and a device for sterilizing a container according to which a sterilizing agent which is turned to mist by a mist generation device is mixed with hot air and supplied to inside of a bottle to sterilize the bottle, then sterilized air is blown into the bottle to exhaust the mist to the outside and then a washing liquid is supplied to the inside of the bottle to wash the bottle. This method however requires the mist generation device and an air wash device for supplying sterilized air and, as a result, the sterilizing apparatus becomes large. Besides, sterilization must be continued until minute droplets of the sterilizing agent mist reach all of the surfaces of projections and depressions of the bottle and, as a result, this method cannot settle the problem of the prior art methods that a long period of time is required for sterilization.

PRIOR ART LITERATURE

Patent Literature

Patent Literature 1: WO2003/022689

SUMMARY OF THE INVENTION

Problem to be Solved by the Invention

This invention has been made in view of the above described problems of the method for sterilizing a container in the prior art aseptic filling system. It is an object of the invention to provide a method for sterilizing a container which can reduce the time of sterilizing a container by hydrogen peroxide, decrease the initial and running costs of sterilization, simplify the sterilizing apparatus, decrease space for installing the sterilizing apparatus and reduce load to the environment.

Means for Settling the Problems

According to the present invention, there is provided a method for sterilizing a container comprising a step of injecting hydrogen peroxide aqueous solution, air at the normal temperature and hot air simultaneously into a container and thereby immediately gasifying the hydrogen peroxide aqueous solution which has been turned to minute droplets by the air at the normal temperature to sterilize the inner surface of the container.

In the method for sterilizing a container according to the present invention, it is preferable that
1. the method further comprises a step of exhausting residual gas out of the container by continuing, after sterilizing the container, supply of at least one of the air at the normal temperature and the hot air while suspending supply of the hydrogen peroxide aqueous solution.
2. temperature of the hot air is within a range from 130° C. to 200° C.
3. sterilization of the container is performed while the container is placed in an inverted state.
4. the container is a container made of polyester.
5. sterilization of the container is performed at a temperature below glass transition temperature.
6. sterilization of the container is performed with a single turret.
7. the container is washed with hot water after the sterilization of the container.
8. the container is washed with hot air after the sterilization of the container.
9. the container is washed with hot water after the container is washed with the hot air.
10. the container is washed with circulating hot water.

According to the invention, there is also provided a 3-fluid nozzle used for carrying out the above described method for sterilizing a container comprising a mixing section which mixes hydrogen peroxide aqueous solution with air at the normal temperature and injects the mixture and also comprising a hot air mixing section.

In the 3-fluid nozzle, the mixing section preferably comprises an opening and closing valve for opening and closing a channel of the hydrogen peroxide aqueous solution.

Advantageous Results of the Invention

According to the method for sterilizing a container of the present invention, by injecting hydrogen peroxide aqueous solution, air at the normal temperature and hot air simultaneously into a container, time required for sterilizing containers including polyester containers such as PET bottles and other types of containers can be significantly shortened, the initial and running costs can be reduced, the sterilizing apparatus can be simplified and space for installing the sterilizing apparatus can be decreased.

According to the 3-fluid nozzle used for carrying out the method for sterilizing a container of the present invention, liquid consisting of hydrogen peroxide can be instantly gasified and injected into the container by mixing the liquid with air at the normal temperature and hot air whereby shortening of time required for sterilization of the inner surface of a container can be realized easily.

DESCRIPTION OF EMBODIMENTS OF THE INVENTION

As a result of studies and experiments for settling the above described problems, the inventors of the present invention has found, which has led to the present invention, that by turning hydrogen peroxide aqueous solution to minute droplets by means of air stream at the normal temperature and simultaneously gasifying these minute droplets instantly by means of hot air at a high temperature and injecting the hydrogen peroxide gas into a container, this gas moves in the container at a speed which is much higher than the speed of hydrogen peroxide mist which is an aggregate of minute droplets and uniformly reaches the inner surface of the container even if the container has projections and depressions of a complex configuration with the surprising result that time for sterilization which, for example, has conventionally required about 8 seconds for sterilizing a PET bottle of 500 ml can be shortened to only 1 second.

Embodiments of the invention will now be described with reference to the accompanying drawings.

Containers which are objects of the method of the present invention are preferably polyester containers such as PET bottles but the present invention is applicable also to other types of containers such as containers made of resin or paper. As to contents of containers to which the present invention can be applied, there is no particular limitation, that is, contents of the container may be food including drinks and jam, seasonings such as mirin (sweet sake) and sauses, cosmetics or drugs.

According to the present invention, hydrogen peroxide aqueous solution, air at the normal temperature and hot air injected simultaneously into a container whereby hydrogen peroxide aqueous solution which has been turned to minute droplets by the air at the normal temperature is immediately gasified to sterilize the inside of the container. For this reason, in the present invention, it is necessary to inject hydrogen peroxide aqueous solution, air at the normal temperature and hot air simultaneously from a single nozzle. For realizing this, various methods and devices can be conceived. As the simplest device, the method of the present invention can be carried out by using a 3-fluid nozzle about which an example is shown in FIG. 1.

The 3-fluid nozzle first turns liquid to minute droplets and then instantly gasifies these minute droplets by hot air and injects the gas from a single nozzle to cause the gas to contact the inside surface of the container and thereby increase the surface temperature of the inside surface of the container to a necessary temperature. The 3-fluid nozzle therefore has the feature that it can gasify liquid to sterilize the inside surface of the container without employing a large scale equipment and, for this reason, the 3-fluid nozzle is the most preferable device for realizing the method of the present invention.

Figure 1:
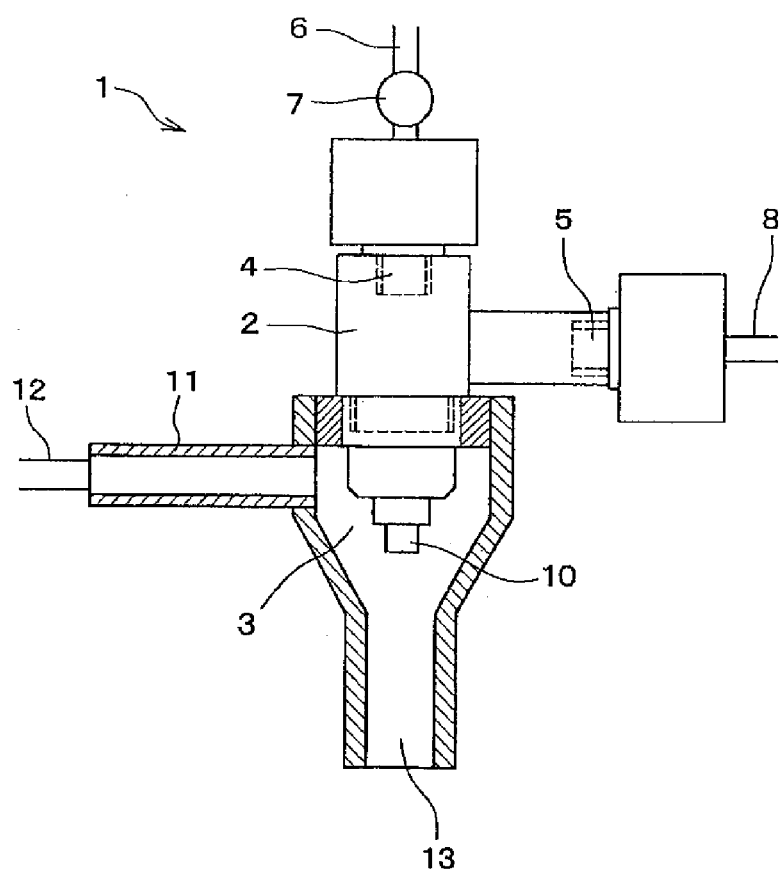
FIG. 1 is a partially sectional view showing an embodiment of a 3-fluid nozzle.

FIG. 1 shows an example of the 3-fluid nozzle. The lower half of the nozzle is shown in section. The 3-fluid nozzle 1 has a mixing section 2 which mixes hydrogen peroxide aqueous solution with air at the normal temperature and injects the mixture and a hot air mixing section 3 provided below the mixing section 2. In the upper portion of the mixing section 2, there is provided a hydrogen peroxide supply nozzle 4 for supplying hydrogen peroxide aqueous solution at a predetermined flow speed. On one side of the mixing section 2, there is provided an air-at-the-normal-temperature supply nozzle 5 for injecting air at the normal temperature at a predetermined speed. The hydrogen peroxide supply nozzle 4 is connected to an unillustrated hydrogen peroxide aqueous solution supply source via a connecting pipe 6. An opening and closing valve 7 is provided at a base portion of the connecting pipe 6. The air-at-the normal-temperature supply nozzle 5 is connected to an unillustrated air-at-the-normal-temperature supply source via a connecting pipe 8. For convenience of illustration, the opening and closing valve 7 is shown as being located above the mixing section 2. The position of the valve 7 is not limited to the illustrated one but valve 7 may alternatively be located immediately above the hydrogen peroxide supply nozzle 4 in the mixing section 2.

Since the mixing section 2 of the 3-fluid nozzle 1 has the opening and closing valve 7 which opens and closes the channel of hydrogen peroxide aqueous solution, by closing the channel of hydrogen peroxide aqueous solution after completion of sterilization of a container to stop supply of hydrogen peroxide aqueous solution while continuing supply of at least air at the normal temperature or hot air, residual gas can be exhausted out of the container easily.

Hydrogen peroxide aqueous solution flowing down from the hydrogen peroxide supply nozzle 4 is turned to minute droplets by means of air at the normal temperature which is injected from the air-at-the-normal-temperature supply nozzle 5 and the minute droplets are injected from an outlet 10 in the lower portion of the mixing section 2.

The hot air mixing section 3 has a hot air supply nozzle 11 on one side of the section 3. The hot air supply nozzle 11 is connected to an unillustrated hot air supply source via a connecting pipe 12. The hot air supply nozzle 11 injects hot air at a temperature within a range from 130° C. to 200° C. at a predetermined speed. The minute droplets of hydrogen peroxide injected from the outlet 10 in the lower portion of the mixing section 2 are instantly gasified to hydrogen peroxide gas by this hot air at a high temperature and the hydrogen peroxide gas is injected into the container from a gas injection opening 13 at the lower end of the hot air mixing section 3.

As described above, the nozzle used for carrying out the method for sterilizing a container of the present invention is a 3-fluid nozzle 1 comprising a mixing section 2 which mixes hydrogen peroxide aqueous solution with air at the normal temperature and injects the mixture and also comprises a hot air mixing section 3. By inserting a single nozzle into a container, sterilization of the inner surface of the container and exhaust of gas can be continuously conducted. Further, by using this nozzle, a mist generation device for generating mist of hydrogen peroxide aqueous solution can be omitted, costs can be saved and the apparatus can be simplified.

By setting the temperature of the hot air within a range from 130° C. to 200° C., minute droplets of hydrogen peroxide aqueous solution can be gasified instantly and completely and, moreover, in a case where the container is a polyester container such as a PET bottle which has excellent transparency and shock-proof property, deformation due to heat can be prevented.

Hydrogen peroxide gas at a high temperature which has been injected into the container in this manner reaches all inner surfaces of the container at a high speed. In the meanwhile, the container is heated with the high temperature gas and a sterilizing effect is produced by this heating of the container. For these reasons, sterilization in the container is completed in a short period of time. After completion of sterilization, by closing the opening and closing valve 6 provided in the mixing section 2 in the state that the gas outlet 13 of the 3-fluid nozzle 1 is inserted in the container while supply from at least one of the air-at-the normal-temperature supply nozzle 5 and the hot air supply nozzle 11 is continued, hydrogen peroxide gas remaining in the container is exhausted out of the container easily. Thus, sterilization and exhaust of gas are completed substantially by a single process with the 3-fluid nozzle 1 of a single unit being inserted in the container and, therefore, exhaust of residual gas after completion of sterilization can also be completed in a short period of time and, as a result, these processes can be completed within a period of time when the container remains in a single turret.

In a case where the container is a polyester container such as a PET bottle, the above described sterilization of the container must be performed at a temperature below glass transition temperature for preventing deformation of the container. As a result of an experiment, it has been found that, when hydrogen peroxide gas at 170° C. is injected a second into a PET bottle of 500 ml, the bottle itself maintains a temperature within a range from 45° C. to 70° C. and no deformation of the bottle takes place.

It is preferable to wash the container after completion of sterilization of the container by hydrogen peroxide gas and subsequent exhaust of residual gas because such washing can improve the sterilization effect and also wash away foreign materials. In case of conducting washing of the container, exhaust of residual gas may be omitted and, by this omission, further reduction of the space for installing the sterilizing apparatus and shortening of the sterilization time can be achieved.

Figure 2:
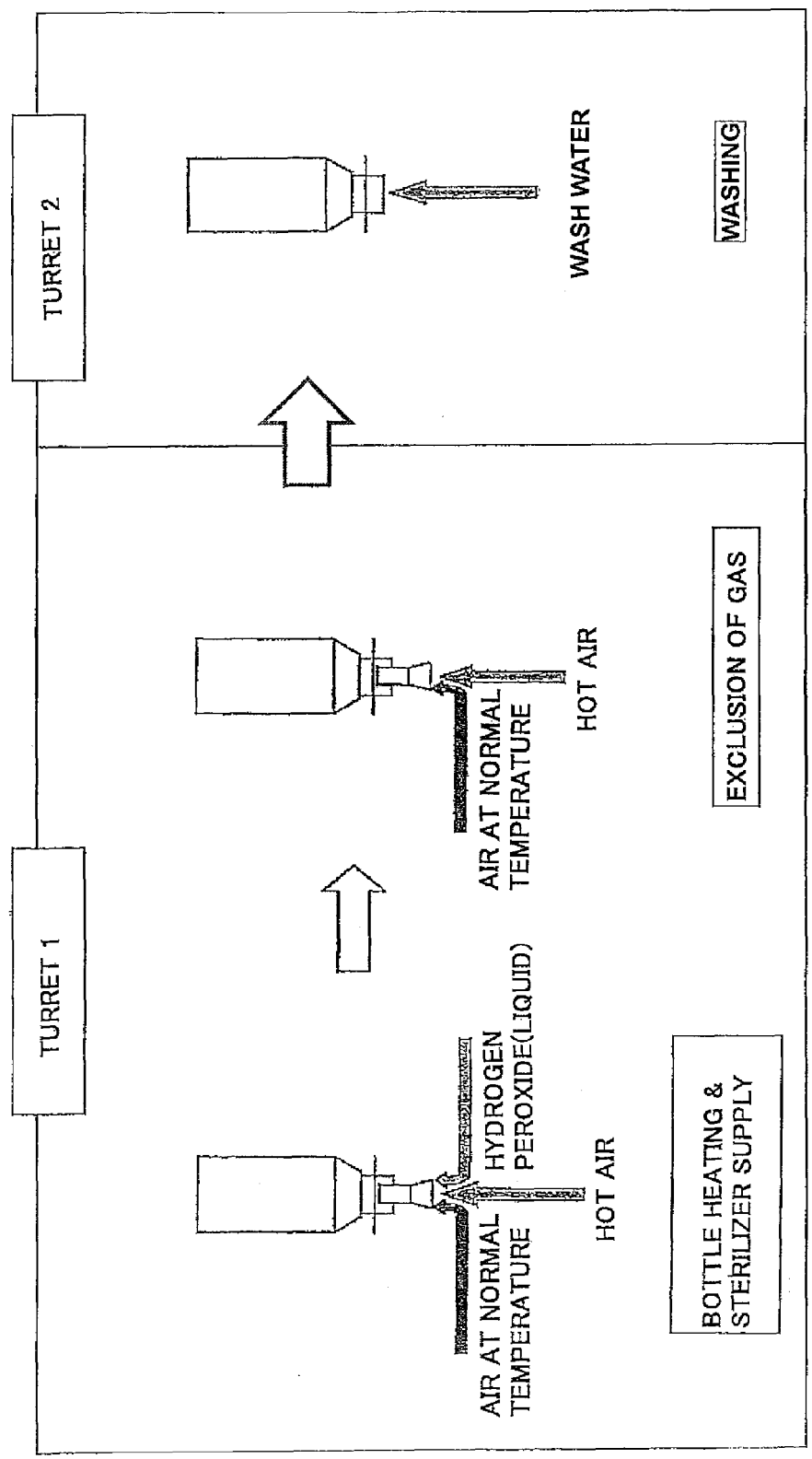
FIG. 2 is an explanatory view showing an embodiment of the present invention.

FIG. 2 is an explanatory view schematically showing an embodiment in which residual gas is exhausted after the sterilization and subsequently the container is washed with hot water.

In the first turret, by completing the above described sterilization and exhaust of residual gas with the container being in an inverted state, the container is carried in the inverted state to the container washing process which is performed with the container being in an inverted state for facilitating easy exhaust of wash water and provision of a container inverting device can thereby be obviated. Besides, by carrying out sterilization and exhaust of gas with a single turret, further reduction of costs, simplifying of the apparatus and reduction of space for installing the apparatus can be achieved.

In the second turret, wash water which is hot water at a temperature within a range from 40° C. to 95° C., preferably within a range from 60° C. to 90° C., is injected from a wash water nozzle into the inverted container to wash the inside of the container. Even when bacteria and foreign materials have remained unexhausted in the container in the residual gas exhaust process, they are washed away from the container by this washing process. Wash time is 1 second to 10 seconds, preferably 3 seconds to 5 seconds. If the wash period is less than 1 second, wash will become insufficient whereas if the wash time exceeds 10 seconds, running cost will increase and load to the environment due to use of energy required for making hot water will increase. For example, wash time required for washing a PET bottle of 500 ml with hot water at 85° C. is about 3 seconds.

This washing with hot water is particularly effective in a case where the container is a polyester container because hydrogen peroxide used for sterilization tends to adsorb onto the inner surface of a polyester container such as a PET bottle. It is preferable to use circulating hot water for further reducing the running cost and also reducing load to the environment.

It is also possible to perform washing after sterilization of the container and exhaust of residual gas by injecting hot air at a temperature within a range from 130° C. to 200° C., preferably within a range from 160° C. to 190° C. into the container. This process is particularly effective when exhaust of residual gas has been made with only air at the normal temperature. The washing process may also be made by using hot water after using hot air. As the hot water used in this case, circulating hot water may preferably be used. In this case, a filter may be used for removing impurities. A catalyst may also be used for dissolving a small amount of hydrogen peroxide contained in the container.

By washing the container with hot water after washing the container with hot air, the sterilization effect can further be improved, washing away of impurities can be realized accurately whereby washing can be made more completely.

The above described washing can be made by using sterilized water at the normal temperature and sterilized air at the normal temperature but, from the standpoints of the sterilization effect and washing effect, use of hot water and hot air are preferable.

The container which has finished the processes of sterilizing of the container, exhaust of residual gas and washing is transferred to a filling process at the next stage in which filling of contents into the container and sealing of the container are performed.

Experimental Example

For confirming the sterilizing effect of the present invention, the following experiment was conducted.

As a container for providing an object of sterilization of the experiment, a PET bottle of 500 ml was used. The container was sterilized by using the 3-fluid nozzle shown in FIG. 1 and then the container was washed by using hot water.

As sample bottles to be sterilized, 10 PET bottles of 500 ml were used. As test bacteria, suspension of *Bacillus subtilis* var. *niger* NBRC13721 was adjusted to the predetermined concentration. The suspension was deposited onto the inner surface of each bottle by spraying in an amount of 0.3 ml per bottle so that concentration will become $10^5$ cfu/bottle (initial number of bacteria being $1.0 \times 10^5$ cfu/bottle).

After having the suspension deposited, each bottle was kept in a clean room (CLASS 10000) for 24 hours for drying the inner surface of each bottle.

In sterilization, 30% hydrogen peroxide aqueous solution was fed to the hydrogen peroxide supply nozzle 4 in the mixing section of the 3-flow nozzle at a feed pressure of 0.16 MPa to cause the solution to flow out of the nozzle 4 in a flow amount of 8 g/minute. In the meanwhile, air at the normal temperature of 25° C. was fed to the air-at-the-normal-temperature supply nozzle 5 in the mixing section at an air pressure of 0.4 MPa to cause the air to be injected from the nozzle 5 and thereby turn hydrogen peroxide aqueous solution to minute droplets. Simultaneously, hot air at 170° C. is fed to the hot air supply nozzle 11 at an air pressure of 0.4 MPa to cause hot air to be injected from the nozzle 11 in a flow amount of 380 l/minute to thereby gasify the minute droplets of hydrogen peroxide aqueous solution instantly.

In sterilizing each bottle, the gas outlet 13 of the 3-fluid nozzle was inserted into the bottle by 15 mm from the top plane of each bottle and hydrogen peroxide gas was injected into the bottle for sterilizing the inner surface of the bottle.

Total sterilizing time required for insertion, lowering, holding (suspending), lifting and taking out of the gas outlet 13 was 1 second.

Then, sterilized hot water at 85° C. was injected from a wash water nozzle into the bottle in which sterilization was finished and the bottle was washed for 3 seconds for washing out hydrogen peroxide which adsorbed onto the bottle. For measuring surviving bacteria, 500 mml of sterilized SCD liquid medium was filled in the bottle and the bottle was sealed with a sterilized cap.

This bottle was kept at 30° C. for seven days. A sample bottle in which turbidity was observed was labeled as being positive (+) and a sample bottle in which turbidity was not observed was labeled as being negative (−).

As a result of the measurement, all of the ten sample bottles proved to be negative (−). Thus, the sterilizing effect was recognized to be 6.0 D or over.

The invention claimed is:

1. A 3-fluid nozzle used for sterilizing an inner surface of a container, comprising a mixing section and a hot air mixing section, said mixing section comprising:
  a. a hydrogen peroxide supply nozzle at an upstream portion of the mixing section for supplying hydrogen peroxide aqueous solution to the mixing section, said hydrogen peroxide supply nozzle comprising an opening and closing valve that opens and closes a channel of hydrogen peroxide aqueous solution that is supplied to the mixing section,
  b. an air-at-the-normal-temperature supply nozzle at an intermediate portion of the mixing section for supplying air at the normal temperature to the mixing section, and
  c. an outlet at a downstream portion of the mixing section for injecting the mixture of the hydrogen peroxide aqueous solution and the air-at-the-normal-temperature into an upstream portion of a hot air mixing section; and said hot air mixing section comprising:
  a. a hot air supply nozzle that is provided on an intermediate portion of the hot air mixing section for supplying hot air to the hot air mixing section, and
  b. an outlet at a downstream portion of the hot air mixing section, wherein the hydrogen peroxide aqueous solution, the air at the normal temperature and the hot air are simultaneously injected into the container from the hot air mixing section, thereby immediately gasifying the hydrogen peroxide aqueous solution.

* * * * *